US008147868B2

(12) United States Patent
Ohuchi et al.

(10) Patent No.: US 8,147,868 B2
(45) Date of Patent: Apr. 3, 2012

(54) PHYSIOLOGICALLY ACTIVE POLYPEPTIDE- OR PROTEIN-ENCAPSULATING POLYMER MICELLES, AND METHOD FOR PRODUCTION OF THE SAME

(75) Inventors: Miho Ohuchi, Kashiwa (JP); Mitsunori Harada, Kashiwa (JP); Yuko Amano, Kashiwa (JP); Yasuki Kato, Kashiwa (JP)

(73) Assignee: Nanocarrier Co., Ltd., Chiba (JP)

( * ) Notice: Subject to any disclaimer, the term of this patent is extended or adjusted under 35 U.S.C. 154(b) by 324 days.

(21) Appl. No.: 12/309,498

(22) PCT Filed: Apr. 25, 2007

(86) PCT No.: PCT/JP2007/059404
§ 371 (c)(1),
(2), (4) Date: Jan. 20, 2009

(87) PCT Pub. No.: WO2008/010341
PCT Pub. Date: Jan. 24, 2008

(65) Prior Publication Data
US 2009/0291130 A1 Nov. 26, 2009

(30) Foreign Application Priority Data
Jul. 18, 2006 (JP) .................................. 2006-195410

(51) Int. Cl.
A61K 9/127 (2006.01)
A61K 38/00 (2006.01)
(52) U.S. Cl. ......................................... 424/450; 514/1.1
(58) Field of Classification Search .................... None
See application file for complete search history.

(56) References Cited

U.S. PATENT DOCUMENTS

| 5,449,513 | A | 9/1995 | Yokoyama et al. | |
|---|---|---|---|---|
| 6,090,925 | A * | 7/2000 | Woiszwillo et al. | 530/410 |
| 2001/0000510 | A1 | 4/2001 | Sakurai et al. | |
| 2004/0138095 | A1 | 7/2004 | Soula et al. | |
| 2006/0110356 | A1 | 5/2006 | Kataoka et al. | |
| 2006/0269613 | A1 * | 11/2006 | Ogawa et al. | 424/490 |

FOREIGN PATENT DOCUMENTS

| EP | 0 721 776 A1 | 7/1996 |
|---|---|---|
| EP | 1 084 172 | 3/2001 |
| EP | 1 230 934 A1 | 8/2002 |
| EP | 1 084 172 B1 | 7/2003 |
| EP | 1 666 031 A1 | 6/2006 |
| JP | 8-188541 | 7/1996 |
| JP | 2690276 | 8/1997 |
| JP | 2694923 | 9/1997 |
| JP | 2690276 | 12/1997 |
| JP | 2694923 | 12/1997 |
| JP | 2777530 | 5/1998 |
| JP | 11-269097 | 10/1999 |
| JP | 2001-146556 | 5/2001 |
| JP | 2004-525939 | 8/2004 |
| JP | 2005-8614 | 1/2005 |
| JP | 2005-336402 | 12/2005 |
| JP | 2006-321763 | 11/2006 |
| WO | WO 99/61512 | 12/1999 |
| WO | WO 02/078677 A1 | 10/2002 |
| WO | WO 2004/105799 A1 | 12/2004 |
| WO | WO 2005/023230 | 3/2005 |
| WO | WO 2005/023230 A1 | 3/2005 |

OTHER PUBLICATIONS

Storm, Gert et al., "Surface modification of nanoparticles to oppose uptake by the mononuclear phagocyte system," Advanced Drug Delivery Reviews 17 (1995), pp. 31-48.
Murakami, Hideki et al., "Influence of the degrees of hydrolyzation and polymerization of poly(vinylalcohol) on the preparation and properties of poly(DL-lactide-co-glycolide) nanoparticle," International Journal of Pharmaceutics, 149 (1997), pp. 43-49.
Hiroshi, Kikuciii, Drug Metabolism & Physicochemical Property Research Laboratory, *Daiichi Pharmaceutical Co., Ltd.*, Pharm Tech Japan, vol. 19, No. 1, (2003), pp. 99-110.
Uchino, H., et al., "Cisplatin-incorporating polymeric micelles (NC-6004) can reduce nephrotoxicity and neurotoxicity of cisplatin in rats," British Journal of Cancer (2005) 93, pp. 678-687.
Hamaguchi, T., et al., NK105, a paclitaxel-incorporating micellar nanoparticle formulation, can extend in vivo antitumor activity and reduce the neurotoxicity of paclitaxel, British Journal of Cancer (2005) 92, pp. 1240-1246.
Search Report for International Patent Application No. PCT/JP2007/059404 dated Jul. 17, 2007.
Chemical Abstracts, 2005, 144:397955 & Collette, Floraine et al., Triblock copolymers self-assembled in vesicles: Applications to the oral delivery of insulin, PMSE Preprints, 2005, vol. 93, p. 439-440 (on Order).
Adv. Drug Deliv. Rev. 17, 31-48 (1995) (on Order).
Int. J. Pharm. 149, 43-49 (1997) (on Order).
Pharm. Tech. Japan 19, 99-110 (2003) (on Order).
Br. J. Cancer 93, 678-697 (2005) (on Order).
Br. J. Cancer 92, 1240-1246 (2005) (on Order).

* cited by examiner

*Primary Examiner* — Janet Epps-Smith
(74) *Attorney, Agent, or Firm* — Christie, Parker & Hale, LLP.

(57) ABSTRACT

The invention provides a physiologically active polypeptide- or protein-encapsulating polymer micelle composition derived from a block copolymer comprising hydrophilic segments and hydrophobic segments.

9 Claims, 5 Drawing Sheets

PHYSIOLOGICALLY ACTIVE POLYPEPTIDE- OR PROTEIN-ENCAPSULATING POLYMER MICELLES, AND METHOD FOR PRODUCTION OF THE SAME

CROSS-REFERENCE TO RELATED APPLICATION

This application is a National Phase Patent Application and claims the priority of International Application Number PCT/JP2007/059404, filed on Apr. 25, 2007, which claims priority of Japanese Patent Application Number 2006-195410, filed on Jul. 18, 2006.

TECHNICAL FIELD

The present invention relates to polymer micelles containing physiologically active polypeptides or proteins at a high content, and which can be biologically administered and are stable in vivo.

BACKGROUND ART

Advances in genetic engineering techniques have allowed numerous physiologically active polypeptides and proteins to be provided in a stable manner by cell culturing methods, for application in the treatment or prevention of diseases. Such polypeptides, however, generally have a short half-life in vivo due to their extremely rapid enzymolysis, metabolism and the like, and in most cases it has not been possible to obtain satisfactory effects when they are administered as drugs. A great deal of research has been conducted to date toward solving this issue, with focus on modification of the polypeptides and proteins with polymers or their sustained-release formulations.

For example, polyethylene glycolation is a polymer modification technique currently used for clinical purposes. Extension of in vivo half-life has been achieved for interferon and the like, thus allowing some degree of sustained effect. This has resulted in less frequent administration and thus reduced burden on patients, but such polymer-modified proteins generally exhibit lower activity due to the modification, and it has been difficult to control the modification sites and modification rates in a reproducible manner.

Microcapsules are also currently used in the clinic as a sustained-release technology. This technology is implemented by employing in vivo-degradable polylactic acid or polylactic acid/glycolic acid copolymer as the base for inclusion of a drug into fine particles. However, the particle size is usually in the micrometer range and is not suitable for intravenous administration. Microcapsules with particle sizes reduced to nanosize have been reported, which are subjected to surface modification to control their uptake into the reticuloendothelial system of the liver or spleen following intravenous administration (Adv. Drug Deliv. Rev. 17, 31-48 (1995)). However, the particle sizes obtained by such methods are at minimum a few hundred nanometers (Int. J. Pharm. 149, 43-49 (1997)), while the surface modification is laborious and it has also been difficult to control the organ distribution in a reproducible manner.

Liposomes using phospholipids may also be mentioned as examples of sustained-release technology currently used in the clinic (Pharm. Tech. Japan 19, 99-110 (2003)). The advantage of liposomes is their low toxicity and antigenicity, because phospholipids are biological substances, and the fact that altering the lipid composition allows encapsulation of numerous bioactive substances such as water-soluble drugs, fat-soluble drugs, macromolecules, proteins, nucleic acids and the like. However, such liposomes do not necessarily have adequate drug retention properties. Specifically, the amounts of drugs that can be encapsulated per unit liposome formulation are currently inadequate and more efficient methods are desired. In addition, the problems such as insufficient stability in vivo and difficulty of industrial production have still not been satisfactorily overcome.

Polymer micelles may be mentioned as a sustained-release technology that is currently being investigated in the clinic as a means of solving these problems (Br. J. Cancer 93, 678-697 (2005), Br. J. Cancer 92, 1240-1246 (2005)). Polymer micelles can be produced using block copolymers composed of hydrophilic polymers and hydrophobic polymers. In water, these block copolymers generally form polymeric micelles with the core comprising of hydrophobic segments, and therefore exhibit excellent properties in terms of fat-soluble drug encapsulation, solubilization and sustained release. (Japanese Patent Publication No. 2777530).

Such polymer micelles are also studied for encapsulation and sustained release of water-soluble drugs. For example, one method of encapsulating adriamycin as a water-soluble compound into polymer micelles involves chemical linkage of the drug to the side chains of the hydrophobic polymer (Japanese Patent Publication No. 2694923). Other alternative methods have also been disclosed for efficient encapsulation by introducing electrostatic interaction between polymer micelles and a peptide, such as a method in which negatively charged functional groups are introduced into the side chains of hydrophobic segments in a block copolymer, for drugs with chargeable substances such as a positively charged basic peptides (Japanese Patent Publication No. 2690276), or a method in which a biodegradable polymer with a carboxyl group, such as polylactic acid or poly(lactic-co-glycolic acid), is added (WO2005/023230). However, these cannot be applied for water-soluble drugs with large molecular weights, and especially proteins and polypeptides. Japanese Patent Publication No. 2690276 discloses examples of encapsulating proteins into micelles. However, the micelles themselves are poorly stable and, when actually administered to the body, are believed to undergo an immediate breakdown, because they have no hydrophobic portions and form only under electrical charge.

A method for stabilizing micelles encapsulating polyelectrolytes has been disclosed, wherein polyion complex micelles with a core-shell structure, formed of a polyelectrolyte and a block copolymer containing hydrophilic and electrically charged segments, have at least one thiol group carried on the electrically charged segments forming the core so that stability is enhanced by crosslinking with disulfide bonds between the electrically charged segments, via the thiol groups they carry (Japanese unexamined Patent Publication (Kokai) No. 2001-146556). During actual use, however, after administration by intravenous injection, the micelles dissociate due to dilution or interaction with serum proteins or undergo interaction with proteins having SS bonds in the molecules. These interactions lead to inactivation of the proteins and destabilization of the is micelles. Therefore, this method cannot be applied for most proteins or polypeptides.

In order to increase the therapeutic effects of physiologically active polypeptides and proteins it is necessary to provide polymer micelles that stably and efficiently encapsulate the physiologically active polypeptides and proteins while allowing their release in a controlled manner, as explained above, but at the current time no such micelles exist that elicit a low immune response and that can be applied to a wide range of physiologically active polypeptides and proteins.

The following techniques have also been proposed to date in an attempt to fulfill the specifications mentioned above, in order to increase the therapeutic effects of physiologically active polypeptides and proteins, but not all of them have been successful.

(A) Japanese Unexamined Patent Publication (Kohyo) No. 2004-525939 relates to a colloidal suspension of nanoparticles, based on polyamino acid blocks and polyalkylene glycol-type hydrophilic polymer blocks, such as polyethylene glycol (PEG). Since formation of drug (protein or polypeptide) nanoparticles is based on adsorption of the drug onto nanoparticles, the protein or polypeptide is present on the nanoparticle surfaces. Specifically, it is believed that attack by digestive enzymes in the body causes rather rapid decomposition of the protein or other substance on the nanoparticle surfaces, resulting in its inactivation. In addition, since the isoelectric points of the proteins and polypeptides that are to be encapsulated are not considered in forming the nanoparticles, the release may be relatively rapid, making it impossible to obtain a long-lasting effect.

(B) European. Patent Publication No. EP1084172B1 relates to delivery of nucleic acids, in particular, using palmitoyl poly-L-lysine polyethylene glycol or palmitoyl poly-L-ornithine polyethylene glycol, in the presence of cholesterol. The particle sizes of the fine particles obtained by this technique are a few hundred nanometers at the smallest, and since they rapidly accumulate in the reticuloendothelial system after intravenous administration, they cannot easily produce long-lasting effects.

(C) Japanese Unexamined Patent Publication (Kokai) No. 11-269097 relates to fine particles with functions such as organ directivity and sustained release, of which the base is a block copolymer comprising a biodegradable polymer as hydrophobic segments and polyamino acid as hydrophilic segments. This strategy is characterized by using biodegradable polyamino acid as the hydrophilic segments, but compared to polyethylene glycol, it is expected to have higher immunogenicity and increased interaction with serum proteins after intravenous administration, leading to shorter retention in blood circulation, making it impossible to obtain a long-lasting effect.

(D) U.S. Pat. No. 6,090,925 discloses a method in which an acetate or phosphate buffering solution containing polyethylene glycol and polyvinylpyrrolidone is added to an aqueous solution of a low molecular compound or peptide which is to be encapsulated, and then a polymer such as serum albumin having an isoelectric point near the pH of the buffering solution is added thereto and microparticles are formed by heating and cooling steps. Because this method includes a heating step at about 70° C., it is considered poorly suitable for heat labile proteins.

DISCLOSURE OF THE INVENTION

Besides the numerous basic physiologically active polypeptides and proteins there also exist a large number of polypeptides and proteins with weakly acidic to neutral isoelectric points, such as interferon-α, G-CSF and insulin. At the current time there does not exist a polymer micelle composition that can be applied for such a wide range of physiologically active proteins or peptides, that allow them to be stably and efficiently encapsulated and released at a controlled rate. It is therefore an object of the present invention to provide a block copolymer composition satisfying the conditions mentioned above, as well as a method for its production.

As a result of much diligent research conducted in light of the current circumstances explained above, the present inventors have discovered that physiologically active polypeptides and proteins can be efficiently encapsulated in polymer micelles by using a block copolymer comprising hydrophilic segments composed of polyethylene glycol, and hydrophobic segments composed of a polyamino acid selected the group consisting of acidic amino acids, hydrophobic derivatives thereof and mixtures of said acidic amino acids and said hydrophobic derivatives. Furthermore, by adjusting the pH used for preparation of the polymer micelles in consideration of the isoelectric points of the physiologically active polypeptides and proteins, we successfully accomplished more efficient encapsulation. The present inventors have completed this invention upon finding that this method can be applied for numerous physiologically active polypeptides and proteins regardless of their acidity or basicity, that modifying the block copolymer can contribute to hydrophobic interaction between the hydrophobic segments and the polypeptide or protein, thus allowing the encapsulation efficiency and release rate of the drug to be improved, and in particular that the structure of the hydrophobic side-chains in the block copolymer contributes significantly to the drug release rate.

The present invention encompasses the following aspects.

[1] A polymer micelle composition encapsulating physiologically active polypeptides or proteins and being composed of a block copolymer comprising hydrophilic segments composed of polyethylene glycol, and hydrophobic segments composed of a polyamino acid selected from among acidic amino acids, their hydrophobic derivatives and mixtures of acidic amino acids and their hydrophobic derivatives.

[2] A composition according to [1] above, wherein the hydrophobic derivatives of acidic amino acids are acidic amino acid alkyl esters or acidic amino acid alkylamides.

[3] A composition according to [1] above, wherein the acidic amino acid is aspartic acid or glutamic acid.

[4] A composition according to [1] above, wherein the block copolymer has the following formula (I) or (II):

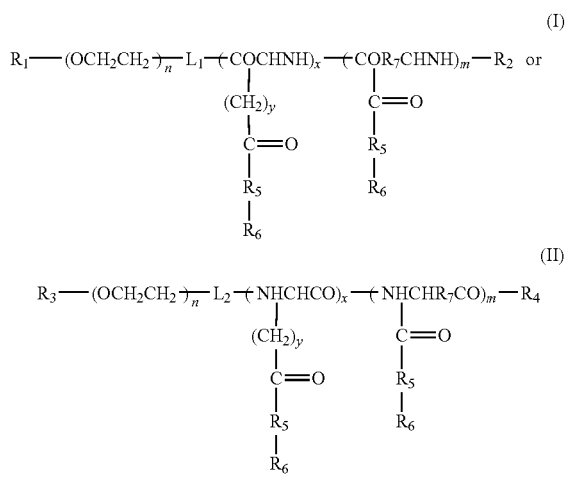

wherein, $R_1$ and $R_3$ each independently represent hydrogen or a lower alkyl group either unsubstituted or substituted with an optionally protected functional group, $R_2$ represents hydrogen, a saturated or unsaturated $C_1$-$C_{29}$ aliphatic carbonyl group or an arylcarbonyl group, $R_4$ represents hydroxyl, a saturated or unsaturated $C_1$-$C_{30}$ aliphatic oxy or aryl-lower alkyloxy group, $R_5$ represents —O— or —NH—, $R_6$ represents hydrogen, phenyl, —$(CH_2)_4$-phenyl, $C_4$-$C_{16}$ alkyl either unsubstituted or substituted with an amino group or carboxyl group, or benzyl, $R_7$ represents methylene, n represents an integer of 10-2500, x represents an integer of 10-300, m represents an integer of 0-300, with the proviso that when m is present, the (COCHNH) units and ($COR_7CHNH$) units are random, $R_6$ may be selected for each amino acid unit in one block copolymer and is randomly present, but hydrogen as $R_6$ constitutes less than 60% of the total $R_6$, y represents an integer of 1 or 2, $L_1$ represents a linking group selected from the group consisting of —NH—, —O—, —O—Z—NH—, —CO—, —$CH_2$—, —O—Z—S—Z— and —OCO—Z—NH—, where each Z independently represents a $C_1$-$C_6$ alkylene group, and $L_2$ represents a linking group selected from the group consisting of —OCO—Z—CO— and —NHCO—Z—CO—, where Z is a $C_1$-$C_6$ alkylene group.

[5] A composition according to [4] above, wherein the block copolymer has a polyamino acid side chain esterification or amidation rate of 40-100%.

[6] A composition according to any one of [1]-[5] above, wherein the isoelectric point (pI) of the protein or polypeptide is 3-11.5.

[7] A method of preparing a polymer micelle composition according to any one of [1]-[6] above, characterized by comprising a step of mixing the block copolymer with the physiologically active polypeptide or protein, and adjusting the pH of the mixture to a pH different from the isoelectric point (pI) of the physiologically active polypeptide or protein to encapsulate the physiologically active polypeptide or protein into the hydrophobic core region of micelles composed of the block copolymer, wherein the pI of the physiologically active polypeptide or protein, the isoelectric point (pI') of the acidic amino acid and/or its derivative in the hydrophobic segments of the block copolymer, and the pH that is different from the pI, are in the relationship:

$$pI > pH > pI'$$

such that the hydrophobic segments of the block copolymer are negatively charged at the pH while the physiologically active polypeptide or protein is positively charged.

[8] A method according to [7] above, wherein the pH has a difference of at least 1 from the pI of the water-soluble macromolecular drug.

The invention affords the advantage of allowing efficient encapsulation of high-molecular-weight drugs such as physiologically active polypeptides and proteins in polymer micelles, while also permitting control of their release rate.

BEST MODE FOR CARRYING OUT THE INVENTION

Figure 1:
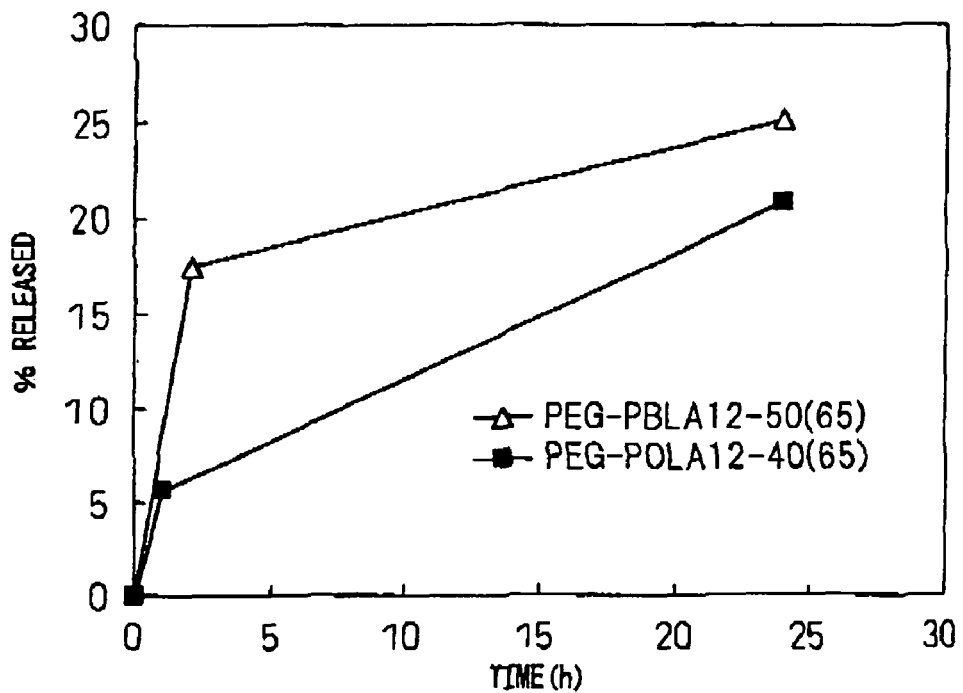
FIG. 1 shows a time-course of IgG release from different IgG-encapsulating polymer micelles.

According to a preferred mode of the invention, it is possible to efficiently encapsulate physiologically active polypeptides or proteins in polymer micelles by using a block copolymer comprising hydrophilic segments composed of polyethylene glycol, and hydrophobic segments composed of a polyamino acid selected from the group consisting of acidic amino acids, hydrophobic derivatives thereof and mixtures of said acidic amino acids and said hydrophobic derivatives.

According to another preferred mode of the invention, it is possible to more efficiently encapsulate physiologically active polypeptides or proteins into the hydrophobic core regions of polymer micelles comprising a block copolymer, by adjusting the pH during preparation of the polymer micelles based on the isoelectric point (pI) of the physiologically active polypeptide or protein to be encapsulated.

For more efficient encapsulation of physiologically active polypeptides or proteins into the polymer micelles, the pH during preparation of the polymer micelles is preferably adjusted to a value different from the pI of the polypeptides or proteins. The pH during preparation of the polymer micelles differs, and more specifically it preferably differs by at least 1, from the pI of the physiologically active polypeptide or protein, within a range such that the physiologically active polypeptide or protein is not denatured. For even more efficient encapsulation of the physiologically active polypeptide or protein, the physiologically active polypeptide or protein preferably has the opposite electrical charge from the hydrophobic segments of the block copolymer, i.e. the sections forming the core of the polymer micelles, at the pH during preparation of the polymer micelles. For example, if the physiologically active polypeptide or protein is positively charged at the pH during preparation of the polymer micelles, the hydrophobic segments of the block copolymer are preferably negatively charged, and if the physiologically active polypeptide or protein is negatively charged, the hydrophobic segments of the block copolymer are preferably positively charged. According to a preferred mode, for example, if the pI of the physiologically active polypeptide or protein, the isoelectric point (pI') of the acidic amino acid and/or its derivative in the hydrophobic segments of the block copolymer and the pH during preparation of the polymer micelles are in the relationship:

$$pI > pH > pI'$$

the hydrophobic segments of the block copolymer will be negatively charged and the physiologically active polypeptide or protein will be positively charged, at that pH. The isoelectric points of the acidic amino acids aspartic acid and glutamic acid are 2.77 and 3.22, respectively.

According to another preferred mode of the invention, specifying the pI of the physiologically active polypeptide or protein allows to select the hydrophobic segments in the block copolymer and to determine appropriately the pH during preparation of the polymer micelles, as suitable for the conditions, so that different physiologically active polypeptides and proteins with a wide range of pI values can be applied. For example, when it is desired to encapsulate a polypeptide or protein having a basic pI, a block copolymer is selected so that the pI' of the acidic amino acid and/or its derivative in the hydrophobic segments is further acidic than that pI, and a pH is appropriately selected between the pI and pI' values for formation of the micelles at that pH, in order to accomplish efficient encapsulation. Conversely, when it is desired to encapsulate a polypeptide or protein having an acidic pI, a block copolymer is selected so that the pI' is further acidic or further basic than that pI, and a pH is appropriately selected between the pI and pI' values for formation of the micelles at that pH, in order to accomplish efficient encapsulation. Preferably, the hydrophobic segments of the block copolymer of the invention have functional groups that are negatively charged in a neutral range, such as pH 5-8. By using such a block copolymer, it is possible to select a pH in a neutral range as the pH during micelle formation, and to avoid exposure of the polypeptide or protein to an extreme acidic or basic millieu.

When considering the pH during preparation of the polymer micelles, the pI of the physiologically active polypeptide or protein and the pI' of the acidic amino acid and/or its derivative in the hydrophobic segments, encapsulation of the physiologically active polypeptide or protein into the polymer micelles may be accomplished by preparing an aqueous mixture of the block copolymer that will form the polymer micelles and the physiologically active polypeptide or protein that is to be encapsulated, and the pH of the mixture is adjusted to a pH that is appropriately selected based on the pI of the drug and the pI' of the acidic amino acid and/or its derivative in the hydrophobic segments of the block copolymer, as explained above.

According to a preferred mode, the block copolymer is dissolved in an appropriate organic solvent, for example, a non-water-miscible organic solvent such as dichloromethane, chloroform, diethyl ether, dibutyl ether, ethyl acetate or butyl acetate, a water-miscible organic solvent such as methanol, ethanol, propyl alcohol, isopropyl alcohol, dimethyl sulfoxide, dimethylformamide, dimethylacetamide, acetonitrile, acetone or tetrahydrofuran, or a mixture thereof. Optionally, the solution may be air-dried to a solid film under a nitrogen gas stream, for example, and the organic solvent removed if necessary by drying, under reduced pressure. An aqueous solution of the water-soluble macromolecular drug that is to be encapsulated is then added to and mixed with the block copolymer that has been treated. Finally, the pH of the mixture is slowly adjusted to the desired pH to form polymer micelles while encapsulating the physiologically active polypeptide or protein therein.

The polymer micelles may be formed, for example, by stirring a mixture of the block copolymer and the physiologically active polypeptide or protein. Formation of the polymer micelles is preferably carried out with application of energy such as sonication. When sonication is used, the formation may be accomplished using a Biodisruptor (Nippon Seiki Co., Ltd.), for example, at Level 4, while cooling on ice. The exposure time is not particularly restricted so long as the physiologically active polypeptide or protein is not denatured, and may be at 1 second intermission for 5 seconds-10 minutes, and preferably 5 seconds-2 minutes.

According to another preferred mode, the dried block copolymer may be worked into a homogeneous powder with a mortar or the like and the physiologically active polypeptide or protein in powder form, or the physiologically active polypeptide or protein dissolved in a small amount of solution, may be added thereto and gently mixed therewith, after which a suitable buffering solution may be added and mixed therewith for between 2 and 24 hours prior to ultrasonic treatment.

According to yet another preferred mode, empty micelles are first prepared and then the physiologically active polypeptide or protein is added, with stirring or stationing, to obtain polymer micelles encapsulating the physiologically active polypeptide or protein. Specifically, a suitable buffering solution may be added to the block copolymer and subjected to ultrasonic treatment to prepare empty micelles as mentioned above, and then the physiologically active polypeptide or protein dissolved in the same buffering solution or the physiologically active polypeptide or protein diluted with the buffering solution may be added thereto and the mixture gently stirred with a stirrer or stationed. The period of time for stirring or stationing is preferably between 2 and 24 hours, and the temperature is preferably from 4° C. to 30° C. and most preferably 4° C. This method is advantageous from the standpoint of stability of the physiologically active polypeptide or protein, since the physiologically active polypeptide or protein is not subjected to ultrasonic treatment. In any case, the suitable buffering solution is preferably one that satisfies the aforementioned relationship between pI and pH.

According to the method of the invention, there are no particular restrictions on physiologically active polypeptides or proteins that can be efficiently encapsulated in the polymer micelles, but preferably they are physiologically active polypeptides or proteins that are water-soluble and have molecular weights of at least 1,500 and preferably at least 2,000. As examples of physiologically active polypeptides and proteins there may be mentioned interferon-$\alpha$, $\beta$ and $\gamma$, erythropoietin, G-CSF, growth hormone, interleukins, TNF, granular leukocyte-macrophage colony-stimulating factor, macrophage colony-stimulating factor, hepatocyte growth factor, the TGF-$\beta$ superfamily, EGF, FGF, IGF-I and the like. This also naturally includes derivatives of the aforementioned proteins, such as those having one or more amino acid substitutions, additions or deletions, so long as their activity is not compromised.

The physiologically active polypeptide or protein will have different isoelectric points, even with the same protein, depending on the presence of sugar chains or its higher-order structure, especially when it is produced by gene recombination. Therefore, when preparing polymer micelles in consideration of the pH during preparation of the polymer micelles, the pI of the physiologically active polypeptide or protein and the pI' of the acidic amino acid and/or its derivative in the hydrophobic segments, it is preferred to set the pH during encapsulation after determining the isoelectric point of the protein or polypeptide that is to be encapsulated, using isoelectric point electrophoresis.

The amount of physiologically active polypeptide or protein used for micellation is not particularly restricted, but will generally be 0.01-50% by weight and preferably 0.1-10% by weight relative to the weight of the water-soluble macromolecular drug with respect to the block copolymer.

Polymers that may be used to form drug-encapsulating polymer micelles according to the invention are block copolymers comprising hydrophilic segments composed of polyethylene glycol, and hydrophobic segments composed of a polyamino acid selected from the group consisting of acidic amino acids, hydrophobic derivatives thereof and mixtures of said acidic amino acids and said hydrophobic derivatives, of which one type may be a hydrophobic segment having a charged functional group. A "hydrophobic segment having a charged functional group" means that the segment as a whole has the hydrophobicity necessary to form the core of the polymer micelles composed of the block copolymer, and that the hydrophobicity is due to hydrophobic sections randomly present in the segments, with negatively charged portions also present in the segment.

The hydrophobic segments of the block copolymer of the invention are capable of firmly holding the macromolecular drug which is to be encapsulated by hydrophobic interaction, and when the hydrophobic segments are charged, they can hold the macromolecular drug through electrostatic interaction as well. The present inventors have found that the structure of the hydrophobic groups in the hydrophobic segments of the block copolymer can control hydrophobic interaction between the encapsulated physiologically active polypeptide or protein and the block copolymer, thus allowing the release rate to be controlled. While it is not our intention to be limited to any particular theory, it is believed that, as will be demonstrated by the examples that follow, the physiologically active polypeptide or protein is held more firmly in the micelle cores if the structure of the hydrophobic groups introduced into the hydrophobic segments of the block copolymer that form the micelles is a linear structure of alkyl groups rather than a planar structure such as benzyl or phenyl, and it is therefore released over a longer period of time. In other words, by modifying the structure of the hydrophobic groups introduced into the hydrophobic segments of the block copolymer, it is possible to adjust the release rate of the physiologically active polypeptide or protein. For example, when it is desired to obtain a higher drug release rate, the introduction of hydrophobic groups with a planar structure such as benzyl or phenyl may be increased, and if it is desired to obtain a lower drug release rate, the introduction of hydrophobic groups with a linear structure such as alkyl groups may be increased. When an intermediate release rate is desired, the ratio of introduction of hydrophobic groups with a planar structure such as benzyl or phenyl and hydrophobic groups with a linear structure such as alkyl groups may be varied to appropriately adjust the release rate.

The following block copolymers are examples of useful block copolymers for the invention.

The hydrophilic segments are composed of poly(ethylene glycol) [or poly(ethylene oxide)], and may optionally include segments derived from polysaccharides, poly(vinylpyrrolidone), polyvinyl alcohol), poly(acrylamide), poly(acrylic acid), poly(methacrylamide), poly(methacrylic acid), poly (methacrylic acid esters), poly(acrylic acid esters), polyamino acids or derivatives thereof, although this is not meant to be restrictive. The polysaccharides referred to here include pullulan, dextran, fructan and galactan.

The hydrophobic segments, on the other hand, may be acidic amino acids, and especially poly(aspartic acid) and/or its derivatives or poly(glutamic acid) and/or its derivatives. Specific but not exclusive examples include poly(acidic amino acid) derivatives such as poly(β-benzyl aspartate), poly(β-benzyl aspartate-co-aspartic acid), poly(β-alkyl aspartate), poly(β-alkyl aspartate-co-aspartic acid), poly(β-allyl aspartate), poly(β-allyl aspartate-co-aspartic acid), poly (β-allyl aspartate), poly(β-aralkyl aspartate-co-aspartic acid), poly(β-aralkyl aspartate), poly(γ-benzyl glutamate), poly(γ-benzyl glutanate-co-glutamic acid), poly(γ-alkyl glutamate), poly(γ-alkyl glutamate-co-glutamic acid), poly(γ-aralkyl glutamate), poly(γ-aralkyl glutamate-co-glutamic acid), poly (β-alkyl aspartamide-co-aspartic acid) and poly(γ-aralkyl-glutamide-co-glutamic acid) segments.

The hydrophobic segments are hydrophobic due to hydrophobic side-chains. As examples of such hydrophobic side-chains there may be mentioned benzyl, phenyl, alkyl, $C_4$-$C_{16}$ alkyl either unsubstituted or substituted with an amino or carboxyl group, and —$(CH_2)_4$-phenyl, as well as any desired combinations thereof. As explained above, since the release rate of the encapsulated drug is adjusted by the structure of hydrophobic side-chains introduced into the poly(amino acid derivative) segments, the hydrophobic side-chains are preferably phenyl or benzyl when a rapid release rate is desired, and the hydrophobic side-chains are preferably alkyl, such as $C_4$-$C_{16}$ alkyl groups, when a slower release rate is desired.

Such poly(amino acid derivative) segments may be modified forms of known polyethylene glycol-co-polyaspartic acid benzyl ester or polyethylene glycol-co-polyglutamic acid benzyl ester. Polyethylene glycol-co-polyaspartic acid benzyl ester or polyethylene glycol-co-polyglutamic acid benzyl ester can be prepared by using polyethylene glycol having one end protected and an amino group at the other end, e.g., MeO-PEG-$CH_2CH_2CH_2$—$NH_2$, as the initiator, and adding N-carboxy-β-benzyl-L-aspartate (BLA-NCA) or N-carboxy-γ-benzyl-L-glutamate (BLG-NCA) to the desired polymerization degree (number of amino acid units) in a dewatered organic solvent for reaction.

After acetylating the ends of the obtained block copolymer with acetyl chloride or acetic anhydride, the benzyl groups are removed by alkaline hydrolysis to form polyethylene glycol-co-polyaspartic acid or polyethylene glycol-co-polyglutamic acid, and then benzyl alcohol is added to the desired esterification ratio in an organic solvent and reaction is conducted in the presence of a condensation agent such as N—N'-dicyclohexylcarbodiimide (DCC) or N—N'-diisopropylcarbodiimide (DIPCI), to obtain a block copolymer having benzyl ester portions.

Reaction with 1-octanol, for example, instead of benzyl alcohol will yield polyethylene glycol-co-polyaspartic acid octyl ester and polyethylene glycol-co-polyglutamic acid octyl ester, while using 1-dodecanol will likewise yield polyethylene glycol-co-polyaspartic acid dodecyl ester and 1-hexadecanol will yield polyethylene glycol-co-polyaspartic acid hexadecyl ester.

When the hydrophobic side-chains are to be introduced by amide bonds, a hydrophobic side-chain with an amino group may be reacted with the carboxyl group of polyethylene glycol-co-polyaspartic acid benzyl ester or polyethylene glycol-co-polyglutamic acid benzyl ester that has been acetylated as described above and then had the benzyl group removed by alkaline hydrolysis, or polyethylene glycol-co-polyaspartic acid benzyl ester may be reacted with a compound containing a primary amine, utilizing aminolysis for conversion of the ester bond an amide bond.

Alternatively, 1-octylamine or the like may first be added to polyethylene glycol-co-polyaspartic acid benzyl ester in an organic solvent to the desired amidation rate and reaction conducted for a prescribed time period, and then 1,8-diaminooctane or the like added in excess of the unconverted benzyl ester, to obtain poly(amino acid derivative) segments having a combination of hydrophobic side-chains with the hydrophobic group ends substituted with amino groups and hydrophobic side-chains without amino group substitution. The rate of esterification or amidation is 40%-100% with respect to the total number of amino acid units. Aspartic acid and glutamic acid may be in optically active forms or mixtures thereof. The hydrophilic segments and hydrophobic segments may be linked by known linking groups, such as ester bonds, amide bonds, imino groups, carbon-carbon bonds or ether bonds.

Block copolymers that are easily produced and can be conveniently used for the invention include those represented by the following formulas (I) and (II).

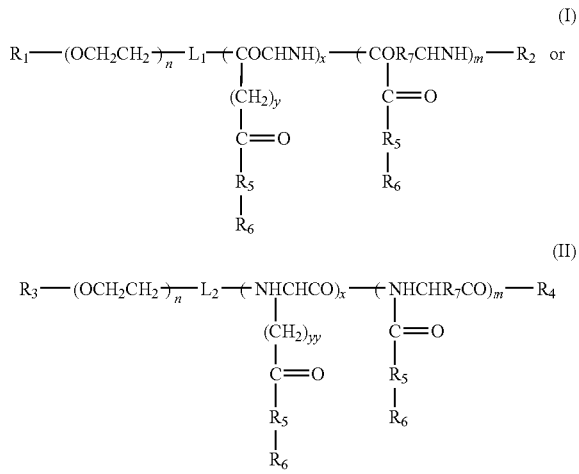

In the formulas, $R_1$ and $R_3$ each independently represent hydrogen or a lower alkyl group either unsubstituted or substituted with an optionally protected functional group, $R_2$ represents hydrogen, a saturated or unsaturated $C_1$-$C_{29}$ aliphatic carbonyl group or an arylcarbonyl group, $R_4$ represents hydroxyl, a saturated or unsaturated $C_1$-$C_{30}$ aliphatic oxy or aryl-lower alkyloxy group, $R_5$ represents —O— or —NH—, $R_6$ represents hydrogen, phenyl, —(CH$_2$)$_4$-phenyl, $C_4$-$C_{16}$ alkyl either unsubstituted or substituted with an amino group or carboxyl group, or benzyl, $R_7$ represents methylene, n represents an integer of 10-2500, x represents an integer of 10-300, m represents an integer of 0-300, with the proviso that when m is present, the (COCHNH) units and (COR$_7$CHNH) units are random, $R_6$ may be selected for each amino acid unit in one block copolymer and is randomly present, but hydrogen as $R_6$ constitutes less than 60% of the total $R_6$, y represents an integer of 1 or 2, $L_1$ represents a linking group selected from the group consisting of —NH—, —O—, —O—Z—NH—, —CO—, —CH$_2$—, —O—Z—S—Z— and —OCO—Z—NH—, where each Z independently represents a $C_1$-$C_6$ alkylene group, and $L_2$ represents a linking group selected from the group consisting of —OCO—Z—CO— and —NHCO—Z—CO—, where Z is a $C_1$-$C_6$ alkylene group.

As optionally protected functional groups there may be mentioned hydroxyl, acetal, ketal, aldehyde, sugar residues, maleimide, carboxyl, amino, thiol and active ester groups. Hydrophilic segments wherein $R_1$ and $R_3$ represent lower alkyl groups substituted with optionally protected functional groups may be obtained by the methods described in WO96/33233, WO96/32434 and WO97/06202, for example. A lower alkyl group is a C7 or lower and preferably C4 or lower straight-chain or branched alkyl group, examples of which include methyl, ethyl, propyl, isopropyl, butyl and isobutyl.

The polymer micelles may be formed, for example, by dissolving the block copolymer and the physiologically active polypeptide or protein in a suitable buffering solution and stirring the mixture, as explained above. Formation of the empty micelle is preferably carried out with application of energy such as sonication. When sonication is used, the formation may be accomplished using a Biodisruptor (Nippon Seiki Co., Ltd.), for example, at Level 4, while cooling on ice. The exposure time is not particularly restricted so long as the physiologically active polypeptide or protein is not denatured, and may be at 1 second intermission for 5 seconds-10 minutes, and preferably 5 seconds-2 minutes. As a different method, the dried block copolymer may be worked into a homogeneous powder with a mortar or the like and the physiologically active polypeptide or protein in powder form, or the physiologically active polypeptide or protein dissolved in a small amount of solution, may be added thereto and gently mixed therewith, after which a suitable buffering solution may be added and mixed therewith for between 2 and 24 hours at 4° C. prior to ultrasonic treatment while cooling on ice.

As yet another method, a suitable buffering solution may be added to the block copolymer and the mixture subjected to ultrasonic treatment to prepare empty micelles as mentioned above, and then the physiologically active polypeptide or protein dissolved in the same buffering solution or the physiologically active polypeptide or protein diluted with the buffering solution may be added thereto and the mixture gently stirred with a stirrer or stationed. The time for stirring or stationing is preferably between 2 hours and 5 days, and the temperature is preferably from 4° C. to 30° C. and most preferably 4° C. This method is advantageous from the standpoint of stability of the physiologically active polypeptide or protein, since the physiologically active polypeptide or protein is not subjected to ultrasonic treatment. In any case, the suitable buffering solution is preferably one that satisfies the aforementioned relationship between pI and pH.

The particle size of the physiologically active polypeptide or protein-encapsulating polymer micelles prepared in this manner is not particularly restricted so long as it is a size permitting in vivo administration, but it is preferably not larger than 10 μm and more preferably not larger than 5 μm. Particularly for intravenous administration use, it is preferably not larger than 500 nm and more preferably not larger than 300 nm. If necessary, an aqueous solution containing the physiologically active polypeptide or protein-encapsulating polymer micelles may be filtered with a hydrophilic filter having a desired pore size.

When the physiologically active polypeptide or protein-encapsulating polymer micelles of the invention are to be administered in vivo, the route of administration may be any desired one such as intravenous administration, subcutaneous administration, intramuscular administration, intraarticular administration, intraperitoneal administration or intraocular administration. As a preferred mode of the invention, the production method may include a step in which various saccharides and/or various polyethylene glycols (e.g. Macrogol) are added to the drug-encapsulating polymer micelle aqueous solution (or the aqueous solution) prior to sterile filtration. Saccharides that may be used include maltose, trehalose, xylitol, glucose, sucrose, fructose, lactose, mannitol, dextrin and the like, and polyethylene glycols that may be used include those with molecular weights of about 1000 to about 35,000, such as Macrogol 1000, 1540, 4000, 6000, 20,000 and 35,000, although these examples are not limitative.

A physiologically active polypeptide or protein-encapsulating polymer micelle formulation of the invention may be lyophilized so long as this does not affect the stability of the encapsulated physiologically active polypeptide or protein. When lyophilized, the dry formulation may be redissolved or reconstituted into a physiologically active polypeptide or protein-encapsulating polymer micelle-containing solution using water or an aqueous solution.

For lyophilization, a saccharide may be added to the solution prior to lyophilization to a final concentration of 0.1-15% (w/v), or polyethylene glycol may be added to a final concentration of 0.5-10% (w/v). The proportion of the block copolymer to the saccharide or polyethylene glycol will normally be 1:1-1:10 or 1:0.5-1:10 by weight.

According to a preferred mode, the ends of the hydrophilic segments may have functional groups capable of bonding to a targetable molecule. As functional groups capable of bonding targetable molecules there may be mentioned hydroxyl, acetal, ketal, aldehyde, carboxyl, maleimide, amino, thiol and active ester groups, without any particular restrictions, and such functional groups may also be protected. As targetable molecules there may be mentioned ligands, antibodies or their functional fragments, proteins, peptides and the like, without any particular restrictions. When a targetable molecule is to be bonded to the functional group, it may be bonded by any known method appropriately selected according to the structure of the molecule.

Examples and comparative examples will now be presented for a more detailed description of the invention.

In the following description, for example, a block copolymer with a PEG average molecular weight of 12,000, a polyamino acid average unit of 40 residues and a benzyl ester introduction ratio of approximately 65% is denoted by 12-40(65) after the name of the block copolymer, while the same with an octyl ester or other introduction ratio of approximately 65% is denoted by 12-40(65). The term "approximately 65%" means about 62%-68%.

EXAMPLES

1) Measurement of Encapsulation Efficiency

Example 1

Human IgG-Encapsulating Micelle Preparation 1

The block copolymer used was polyethylene glycol-co-polyaspartic acid benzyl ester (hereinafter, PEG-PBLA. In this polymer, the aspartic acid residues without benzyl esters are of general formula (I) wherein $R_5$ is —O— and $R_6$ is hydrogen (same hereunder). Also, all of the following block copolymers are of general formula (I) wherein $R_1$ is $CH_3$, $L_1$ is —O—$(CH_2)_3$NH and $R_2$ is $COCH_3$. After precisely weighing out 10 mg of PEG-PBLA 12-50(65) into a glass vial, 1 ml of dichloromethane was added for dissolution. The solution was dried into a film under a nitrogen gas stream, and then further dried for about 1 hour under reduced pressure. To this there was added 62 µL of a 20 mM phosphate buffer (pH 6, 16.5 mg/mL) solution containing purified human IgG (MP Biomedicals Co.) (pI: approximately 8), and then 1.938 mL of 20 mM phosphate buffer (pH 6) or 20 mM TAPS buffer (pH 8) was slowly added while gently stirring at 4° C. After stirring overnight at 4° C., a Biodisruptor (High Power Unit, product of Nissei Corp.) was used for sonication for about 10 seconds (1 second intermission, output: Low) while cooling on ice, and the mixture was subjected to gel filtration (Sepharose® CL-4B, Sigma-Aldrich Corp., ~2ϕ×30 cm). The IgG concentration of each recovered fraction (eluent: 20 mM phosphate buffer (pH 7.4), flow rate: 1.0 mL/min, fraction volume: 1 mL) was assayed using a BCA Protein Assay (Pierce Corp.). The encapsulation efficiency was calculated by the following formula.

$$\text{Encapsulation efficiency (\%)} = \frac{\text{(Protein content in micelle fraction)} \times 100}{\text{Total protein content in all fractions}}$$

The encapsulation efficiency was 94% with preparation at pH 6, and the encapsulation efficiency was 41% with preparation at pH 8. The results indicate that the protein was more efficiently encapsulated by preparing the micelles under pH conditions different from the isoelectric point of the encapsulated protein, than preparing them at near the isoelectric point, based on electrostatic interaction between the protein and PEG-PBLA 12-50(65).

Example 2

Human IgG-Encapsulating Micelle Preparation 2

The block copolymer used was polyethylene glycol-co-polyglutamic acid benzyl ester (hereinafter, PEG-PBLG. In this polymer, the glutamic acid residues without benzyl esters are of general formula (I) wherein $R_5$ is —O— and $R_6$ is hydrogen (same hereunder)). After precisely weighing out 10 mg of PEG-PBLG 12-40(65) into a glass vial, 1 mL of dichloromethane was added for dissolution. The solution was dried into a film under a nitrogen gas stream, and then further dried for about 1 hour under reduced pressure. To this there was added 62 µL of a phosphate buffer solution (pH 6, 16.5 mg/mL) containing purified human IgG (MP Biomedicals Co.) (pI: approximately 8), and then 1.938 mL of 20 mM phosphate buffer (pH 6) or 20 mM TAPS buffer (pH 8) was slowly added while gently stirring at 4° C. After stirring overnight at 4° C., a Biodisruptor (High Power Unit, product of Nissei Corp.) was used for sonication for about 10 seconds (1 second intermission, output: Low), and the mixture was subjected to gel filtration (Sepharose® CL-4B, Sigma-Aldrich Corp., ~2ϕ×30 cm). The IgG concentration of each recovered fraction (eluent: 20 mM phosphate buffer (pH 7.4), flow rate: 1.0 mL/min, fraction volume: 1 mL) was assayed using a BCA Protein Assay (Pierce Corp.). The encapsulation efficiency was calculated by the following formula.

$$\text{Encapsulation efficiency (\%)} = \frac{\text{(Protein content in micelle fraction)} \times 100}{\text{Total protein content in all fractions}}$$

The encapsulation efficiency was 83% with preparation at pH 6, and the encapsulation efficiency was 63% with preparation at pH 8. The results indicate that the protein was more efficiently encapsulated by preparing the micelles under pH conditions different from the isoelectric point of the encapsulated protein, than preparing them at near the isoelectric point, based on electrostatic interaction between the protein and PEG-PBLG 12-40(65).

Example 3

Human IgG-Encapsulating Micelle Preparation 3

The block copolymer used was polyethylene glycol-co-polyaspartic acid octyl ester (hereinafter, PEG-POLA. In this polymer, the aspartic acid residues without octyl esters are of general formula (I) wherein $R_5$ is —O— and $R_6$ is hydrogen (same hereunder)). After precisely weighing out 10 mg of PEG-POLA 12-40(65) into a glass vial, 1 mL of dichloromethane was added for dissolution. The solution was dried into a film under a nitrogen gas stream, and then further dried for about 1 hour under reduced pressure. To this there was added 62 μL of a 20 mM phosphate buffer (pH 6, 16.5 mg/mL) solution containing purified human IgG (MP Biomedicals Co.) (pI: approximately 8), and then 1.938 mL of 20 mM phosphate buffer (pH 6) or 20 mM TAPS buffer (pH 8) was slowly added while gently stirring at 4° C. After stirring overnight at 4° C., a Biodisruptor (High Power Unit, product of Nissei Corp.) was used for sonication for about 10 seconds (1 second intermission, Low) while cooling on ice, and the mixture was subjected to gel filtration (Sepharose® CL-4B, Sigma-Aldrich Corp., ~2ϕ×30 cm). The IgG concentration of each recovered fraction (eluent: 20 mM phosphate buffer (pH 7.4), flow rate: 1.0 mL/min, fraction volume: 1 mL) was assayed by amino acid analysis (AccQ-Tag™, Waters Co.). The encapsulation efficiency was calculated by the following formula.

$$\text{Encapsulation efficiency (\%)} = \frac{(\text{Protein content in micelle fraction}) \times 100}{\text{Total protein content in all fractions}}$$

The encapsulation efficiency was 97% with preparation at pH 6, and the encapsulation efficiency was 24% with preparation at pH 8. The results indicate that the protein was more efficiently encapsulated by preparing the micelles under pH conditions different from the isoelectric point of the encapsulated protein, than preparing them at near the isoelectric point, based on electrostatic interaction between the protein and PEG-POLA 12-40(65).

Comparative Example 1

Human IgG-Encapsulating Micelle Preparation 4

After precisely weighing out 10 mg of PEG-PBLA 12-50 (100) into a glass vial, 1 mL of dichloromethane was added for dissolution. The solution was dried into a film under a nitrogen gas stream, and then further dried for about 1 hour under reduced pressure. To this there was added 62 μL of a 20 mM phosphate buffer (pH 6, 16.5 mg/mL) solution containing purified human IgG (MP Biomedicals Co.) (pI: approximately 8), and then 1.938 mL of 20 mM phosphate buffer (pH 6) or 20 mM TAPS buffer (pH 8) was slowly-added while gently stirring at 4° C. After stirring overnight at 4° C., a Biodisruptor (High Power Unit, product of Nissei Corp.) was used for sonication for about 10 seconds (1 second intermission, output: Low) while cooling on ice, and the mixture was subjected to gel filtration (Sepharose® CL-48, Sigma-Aldrich Corp., ~2ϕ×30 cm). The IgG concentration in the recovered fractions (eluent: 20 mM phosphate buffer (pH 7.4), flow rate: 1.0 mL/min, fraction volume: 1 mL) was assayed using a BCA Protein Assay (Pierce Corp.) The encapsulation efficiency was calculated by the following formula.

$$\text{Encapsulation efficiency (\%)} = \frac{(\text{Protein content in micelle fraction}) \times 100}{\text{Total protein content in all fractions}}$$

The encapsulation efficiency was 22% with preparation at pH 6, and the encapsulation efficiency was 65% with preparation at pH 8. The results indicate that when using PEG-PBLA 12-50(100) which lacks carboxyl groups, electrostatic interaction did not play a part even when the micelles were prepared under pH conditions different from the isoelectric point of the encapsulated protein, and therefore it was difficult to achieve efficient encapsulation of the protein. The protein was encapsulated based on hydrophobic interaction when preparation was at near the isoelectric point.

Comparative Example 2

Human FITC-Labeled IgG-Encapsulating Micelle Preparation

Three block copolymers were used, a polyethylene glycol-polyaspartic acid (average number of residues: approximately 50, non-esterified) block copolymer, PEG-PBLA 12-50(65) and PEG-POLA 12-40(65). After precisely weighing out 20 mg of each polymer into a glass vial, 2 mL of dichloromethane was added for dissolution. The solution was dried into a film under a nitrogen gas stream, and then further dried for about 1 hour under reduced pressure. To this there was added 100 mL of an FITC-labeled human immunoglobulin (FITC-IgG) phosphate buffer solution (Sigma-Aldrich Corp., 20 mg/mL), and then 1.9 mL of 20 mM phosphate buffer (pH 6) was slowly added while gently stirring at 4° C. After further stirring overnight at 4° C., a Biodisruptor (High Power Unit, product of Nissei Corp.) was used for sonication for about 10 seconds (1 second intermission, output: Low) while cooling on ice, and the mixture was subjected to ultracentrifugation (30,000 rpm, 1 hour, 4° C., MLA-130 Rotor by Beckman Coulter). The micelle fraction recovered as precipitation was suspended in 20 mM phosphate buffer (pH 6) and then subjected to gel filtration (Sepharose® CL-4B, Sigma-Aldrich Corp., ~2ϕ×30 cm). The FITC-IgG concentration in each recovered fraction (eluent: 20 mM phosphate buffer (pH 7.4), flow rate: 1.0 mL/min, fraction volume: 1 mL) was assayed using a plate reader (PowerScan® HT, Dainippon Sumitomo Pharma Co., Ltd.) (excitation wavelength: 485 nm±20 mm, emission wavelength: 528 nm±20 nm), and the encapsulation efficiency was calculated by the following formula.

$$\text{Encapsulation efficiency (\%)} = \frac{(\text{Protein content in micelle fraction}) \times 100}{\text{Total protein content in all fractions}}$$

The encapsulation efficiency was 6% when a polyethylene glycol-polyaspartic acid (average number of residues: 50, non-esterified) block copolymer was used. When PEG-PBLA 12-50(65) and PEG-POLA 12-40(65) were used, the encapsulation efficiency was 51% and 60%, respectively. The results indicate that protein can be more efficiently encapsulated by using a polymer comprising overall hydrophobic segments with both hydrophobic substituents and electrically charged groups, suggesting that hydrophobic interaction is also responsible for encapsulation, in addition to electrostatic interaction. These results, when considered in light of the results of Examples 1-3, indicate that the structure of the hydrophobic groups in the hydrophobic segments of the block copolymer do not play a major role in encapsulation efficiency.

Example 4

Preparation of FITC-Labeled Bovine Serum Albumin-Encapsulating Micelles

After precisely weighing out 40 mg of PEG-PBLA 12-50 (65) into a glass vial, 2 mL of dichloromethane was added for dissolution. The solution was dried into a film under a nitrogen gas stream, and then further dried for about 1 hour under reduced pressure. To this there was added 200 µL of an FITC-labeled bovine serum albumin (Sigma-Aldrich Corp.) (pI: approximately 5) aqueous solution (20 mg/mL), and then 3.8 mL of 50 mM citrate buffer (pH 3.5) or 20 mM phosphate buffer (pH 6) was gradually added while gently stirring at 4° C. After further stirring overnight at 4° C., a Biodisruptor (High Power Unit, product of Nissei Corp.) was used for sonication for about 10 seconds (1 second intermission, output: Low) while cooling on ice, and the mixture was subjected to ultracentrifugation (30,000 rpm, 1 hour, 4° C., MLA-130 Rotor by Beckman Coulter). The FITC-labeled bovine serum albumin concentration in the supernatant was assayed using a plate reader (Powerscan® HT, Dainippon Sumitomo Pharma Co., Ltd.) (excitation wavelength: 485 nm±20 nm, emission wavelength: 528 nm±20 nm), and the encapsulation efficiency was calculated by the following formula.

$$\text{Encapsulation efficiency (\%)} = \frac{(\text{Protein content before ultracentrifugation} - \text{protein content of supernatant})}{\text{Protein content before ultracentrifugation}} \times 100$$

The encapsulation efficiency was 16% with preparation at pH 3.5, and the encapsulation efficiency was 7% with preparation at pH 6. The results indicate that the protein was more efficiently encapsulated by preparing the micelles under pH conditions different from the isoelectric point of the encapsulated protein, than preparing them at near the isoelectric point, based on electrostatic interaction between the protein and PEG-PBLA 12-50(65).

Example 5

Preparation of Bovine Hemoglobin-Encapsulating Micelles

After precisely weighing out 20 mg of PEG-PBLA 12-50 (65) into a glass vial, 2 mL of dichloromethane was added for dissolution. The solution was dried into a film under a nitrogen gas stream, and then further dried for about 1 hour under reduced pressure. To this there was added 100 µL of a bovine hemoglobin (Sigma-Aldrich Corp.) (pI: approximately 7) aqueous solution (20 mg/mL), and then 1.9 mL of 20 mM phosphate buffer (pH 6.0) or 20 mM phosphate buffer (pH 7.4) was gradually added while gently stirring at 4° C. After stirring overnight at 4° C., a Biodisruptor (High Power Unit, product of Nissei Corp.) was used for sonication for about 10 seconds (1 second intermission, output: Low) while cooling on ice, and the mixture was subjected to gel filtration (Sepharose® CL-4B, Sigma-Aldrich Corp., ~2φ×30 cm). The hemoglobin concentration in each recovered fraction (eluent: 20 mM phosphate buffer (pH 7.4), flow rate: 1.0 mL/min, fraction volume: 1 mL) was assayed using a plate reader (PowerScan® HT, Dainippon Sumitomo Pharma Co., Ltd.). The encapsulation efficiency was calculated by the following formula.

$$\text{Encapsulation efficiency (\%)} = \frac{(\text{Protein content in micelle fraction}) \times 100}{\text{Total protein content in all fractions}}$$

The encapsulation efficiency was 19% with preparation at pH 6.0, and the encapsulation efficiency was 10% with preparation at pH 7.4. The results indicate that the protein was more efficiently encapsulated by preparing the micelles under more acidic conditions than the isoelectric point of the encapsulated protein, than preparing them under more alkaline conditions than the isoelectric point, based on electrostatic interaction between the protein and PEG-PBLA 12-50(65).

Example 6

Preparation of Recombinant Human Interferon-α-Encapsulating Micelles

On the one hand, after precisely weighing out 7.0 mg of PEG-PBLA 12-50(65) into a glass vial, 0.7 mL of dichloromethane was added for dissolution. The solution was dried into a film under a nitrogen gas stream, and then further dried for about 1 hour under reduced pressure. To this there was added a recombinant human interferon-α (pI: approximately 6.0) PBS solution (IFN-α, FBL Biomedical Laboratories) (0.2 mg/mL 35 µL), and then 200 µL of 0.1 M MES buffer (pH 5.0) was added. The mixture was gently mixed at 4° C. to essentially total dissolution of the polymer, and then 20 mM MES buffer (pH 5.0) was added to a total volume of 1.4 mL and stirring was continued overnight at 4° C. Upon completion of the stirring, the mixture was subjected to ultracentrifugation (30,000 rpm, 1 hour, 4° C., MLA-130 Rotor by Beckman Coulter) and the IFN-α concentration of the supernatant was assayed using an ELISA kit (PBL Biomedical Laboratories).

On the other hand, after precisely weighing out 2.6 mg of PEG-PBLA 12-50(65) into a glass vial, 0.26 mL of dichloromethane was added for dissolution. The solution was dried into a film under a nitrogen gas stream, and then further dried for about 1 hour under reduced pressure. To this there was added the same recombinant human interferon-α PBS solution (0.2 mg/mL 12.5 µL) as before, and then 100 µL of 0.1 M TAPS buffer (pH 8.0) was added. The mixture was gently mixed at 4° C. to essentially total dissolution of the polymer, and then 400 µL of 20 mM TAPS buffer (pH 8.0) was added and stirring was continued overnight at 4° C. Upon completion of the stirring, the mixture was subjected to ultracentrifugation (30,000 rpm, 1 hour, 4° C., MLA-130 Rotor by Beckman Coulter) and the IFN-α concentration of the supernatant was assayed using an ELISA kit (PBL Biomedical Laboratories). The encapsulation efficiency was calculated by the following formula based on the measured values obtained from each test.

$$\text{Encapsulation efficiency (\%)} = \frac{(\text{Protein content at preparation} - \text{protein content of supernatan}) \times 100}{\text{Protein content at preparation}}$$

The encapsulation efficiency was 100% with preparation at pH 5.0, and the encapsulation efficiency was 36% with preparation at pH 8.0. The results indicate that the protein was more efficiently encapsulated by preparing the micelles under more acidic conditions than the isoelectric point of the encapsulated protein, than preparing them under more alkaline conditions than the isoelectric point, based on electrostatic interaction between the protein and PEG-PBLA 12-50(65).

Example 7

Preparation of Papain-Encapsulating Micelles

After precisely weighing out 20 mg of PEG-PBLA 12-40 (65) into a glass vial, 2 mL of dichloromethane was added for dissolution. The solution was dried into a film under a nitrogen gas stream, and then further dried for about 1 hour under reduced pressure. To this there was added 100 μL of a papain (Sigma-Aldrich Corp.) (pI: approximately 8.8) aqueous solution (20 mg/mL), and then 1.9 mL of 20 mM phosphate buffer (pH 6.0) or 20 mM TAPS buffer (pH 8.0) was gradually added while gently stirring at 4° C. After stirring overnight at 4° C., a Biodisruptor (High Power Unit, product of Nissei Corp.) was used for sonication for about 10 seconds (1 second intermission, output: Low) while cooling on ice, and the mixture was subjected to gel filtration (Sepharose® CL-4B, Sigma-Aldrich Corp., ~2φ×30 cm). The papain concentration in each recovered fraction (eluent: 20 mM phosphate buffer (pH 7.4), flow rate: 1.0 mL/min, fraction volume: 1 mL) was assayed using a BCA Protein Assay (Pierce Corp.) The encapsulation efficiency was calculated by the following formula.

$$\text{Encapsulation efficiency (\%)} = \frac{(\text{Protein content in micelle fraction}) \times 100}{\text{Total protein content in all fractions}}$$

The encapsulation efficiency was 27% with preparation at pH 6.0, and the encapsulation efficiency was 9% with preparation at pH 8.0. The results indicate that protein can be more efficiently encapsulated by preparing micelles under pH conditions different from the isoelectric point of the encapsulated protein, than preparing them at near the isoelectric point, based on electrostatic interaction between the protein and PEG-PBLA 12-40(65).

Moreover, the results of the examples described above demonstrate that a wide range of proteins can be efficiently encapsulated in polymer micelles according to the invention.

2) Evaluation of Protein Release Rate from Micelles

Example 8

Evaluation of Release from Human FITC-Labeled IgG-Encapsulating Micelles

The block copolymer used was PEG-PBLA 12-50(65) or PEG-POLA 12-40(50). After precisely weighing out 20 mg of each polymer into a vial, 2 mL of dichloromethane was added for dissolution. The solution was dried into a film under a nitrogen gas stream, and then further dried for about 1 hour under reduced pressure. To this there was added 100 μL of FITC-labeled human immunoglobulin (FITC-IgG) (Sigma-Aldrich Corp., 20 mg/mL), and then 3.9 mL of 20 mM phosphate buffer (pH 6.0) was slowly added while gently stirring. After further stirring overnight at 4° C., a Biodisruptor (High Power Unit, product of Nissei Corp.) was used for sonication for about 10 seconds (1 second intermission, output: Low) while cooling on ice, and the mixture was subjected to ultracentrifugation (30,000 rpm, 4° C., 1 hour) to obtain micelles. The recovered micelles were suspended in 20 mM phosphate buffer (pH 6) and added to bovine serum [final bovine serum concentration: 50% (v/v)], and then incubated at 37° C. In order to evaluate release of the encapsulated FITC-IgG, 1 mL of sample was subjected to gel filtration (Sepharose® CL-4B, Sigma-Aldrich Corp., ~2φ×30 cm) after a predetermined incubation time. The FITC-IgG concentration in each recovered fraction (eluent: 20 mM phosphate buffer (pH 7.4), flow rate: 1.0 mL/min, fraction volume: 1 mL) was assayed using a plate reader (PowerScan® HT, Dainippon Sumitomo Pharma Co., Ltd.) (excitation wavelength: 485 nm±20 nm, emission wavelength: 528 nm±20 nm), and the release rate was calculated by the following formula.

$$\text{Release rate (\%)} = \frac{\text{Protein content of } FITC - \text{labeled human } IgG \text{ fraction} \times 100}{\text{Protein content of micelle fraction recovered by gel filtration applied immediately after mixture with buffering solution}}$$

(The buffering solution was 20 mM phosphate buffer (pH 6).)

The time-course of the release is shown in FIG. 1. These results indicate that the protein encapsulated in the micelles exhibited prolonged release without initial burst, even in the presence of serum. The release rate was thus shown to be dependent on the structure of the hydrophobic groups. Without being constrained by any particular theory, it is believed that a macromolecular drug is held more firmly in the micelle cores if the structure of the hydrophobic groups introduced into the hydrophobic segments of the block copolymer that form the micelles is a linear structure of alkyl groups rather than a planar structure such as benzyl, such that the release occurs in a more controlled manner.

Example 9

Interferon-α Intravenous Administration Test

The block copolymer used was PEG-PBLA 12-50(65) or PEG-POLA 12-40(65). After precisely weighing out 10 mg of the polymer into a vial, 1 mL of dichloromethane was added for dissolution. The solution was dried into a film under a nitrogen gas stream, and then further dried for about 3 hours under reduced pressure. To this there was added a recombinant human interferon-α PBS solution (IFN-α, PBL Biomedical Laboratories) (0.2 mg/mL, 46 μL), and then 200 μL of 0.2 M MES buffer (pH 5.0) was added. The mixture was gently stirred at 4° C. to essentially total dissolution of the polymer, and then 20 mM MES buffer (pH 5.0) was added to a total volume of 2 mL and stirring was continued for a full day at 4° C. The sample was subjected to ultracentrifugation (30,000 rpm, 1 hour, 4° C., MLA-130 Rotor by Beckman Coulter), and the non-encapsulated IFN-α was removed while recovering the precipitated micelles. The micelles were suspended in a 5% glucose aqueous solution and provided for the following animal experiment.

Six-week-old Wistar male rats were divided into groups of 2 rats each, and the test solution was administered through the tail vein at a dosage of 1×10⁶ IU/kg. 5 minutes and 1, 3, 6, 9 and 24 hours after administration, about 0.2 mL of blood was collected from the cervical vein using a heparin-coated syringe. The blood was immediately centrifuged at 13,800 rpm, 4° C. (EF-1300, EC6-Fuge™, Tomy Seiko Co., Ltd.) and the plasma was harvested and stored at −30° C. until analysis. The plasma concentration of interferon-α was determined by a human interferon-α ELISA kit (PBL Biomedical Laboratories).

Figure 2:
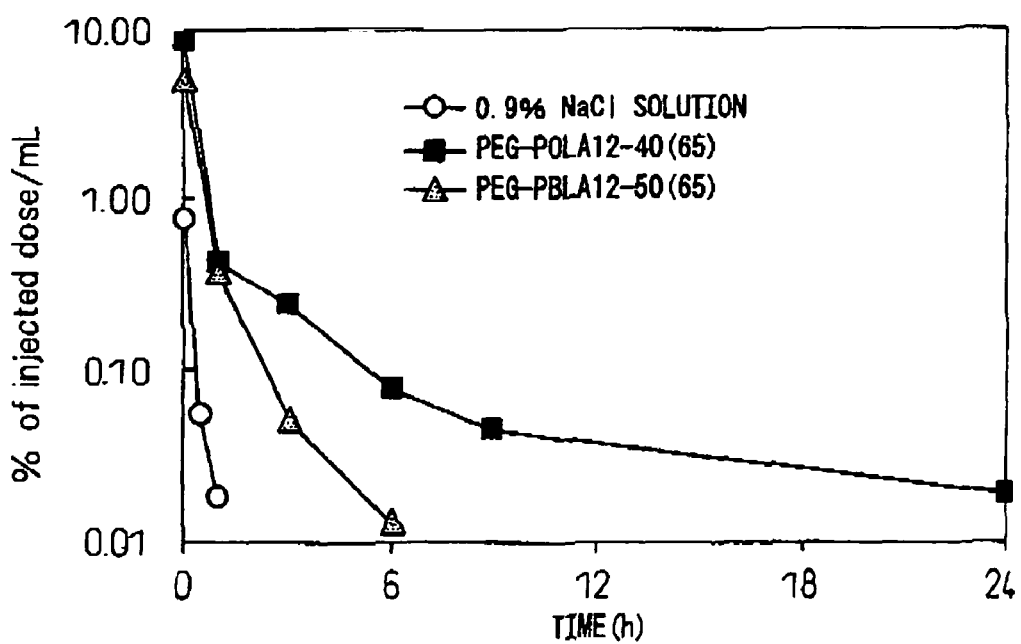
FIG. 2 shows a time-course of interferon-α plasma concentration after in vivo administration of different interferon-α-encapsulating polymer micelles.

The results are shown in FIG. 2. Encapsulation of interferon-α in polymeric micelles improved the retention of plasma concentration. The pharmacokinetic parameters calculated according to a non-compartment model are shown below.

| Pharmacokinetic parameters | 0.9% NaCl solution | PEG-POLA 12-40(65) micelles | PEG-PBLA 12-50(65) micelles |
|---|---|---|---|
| $AUC_{inf}$ (% dose/mL · h) | 0.20 | 7.0 | 3.5 |
| $T_{1/2}$ (h) | 0.11 | 10.4 | 1.3 |
| Cl (mL/h/body) | 491 | 14.4 | 28.9 |
| $MRT_{inf}$ (h) | 0.2 | 3.2 | 0.4 |
| Vss (mL/body) | 81 | 46 | 12 |

Micellation increased the AUC by 17-fold to 35-fold. These results indicate that the protein-encapsulating micelles stay in the blood circulation for a long time without initial burst. Also these results show that the protein release rate in vivo is dependent on the hydrophobic group structure of the block copolymer, similar to the in vitro results.

Example 10

Rat Intravenous Administration Test with FITC-Labeled Lysozyme-Encapsulating Micelles 1) FITC labeling of Lysozyme After dissolving 100 mg of lysozyme (from egg white) (Sigma-Aldrich Corp.) in 2 ml of a 100 mM boric acid buffer (pH 8.5), 170 µL of a 50 mg/mL DMSO solution containing FITC (PIERCE) was added. After stirring at room temperature for 1 hour, the unreacted FITC was removed by gel filtration (PD-10, product of GE Healthcare Bioscience) (eluent: 20 mM sodium phosphate buffer, pH 7.4). After subsequent dialysis against water at 4° C., it was purified by additional gel filtration (Sepharose® CL-4B, Sigma-Aldrich Corp.) (eluent: 20 mM sodium phosphate buffer, pH 7.4).

2) Preparation of FITC-Labeled Lysozyme-Encapsulating Micelles and Rat PK Test

After precisely weighing out 40 mg of the block copolymer PEG-POLA 12-40(65) into a glass vial, 4 mg of FITC-labeled lysozyme (29.2 mg/mL, 137 µL) and then 500 µL of 20 mM sodium phosphate buffer (pH 6.0) were added. After further stirring overnight at 4° C., a Biodisruptor (High Power Unit, product of Nissei Corp.) was used for sonication for about 10 seconds (1 second intermission, output: Low) while cooling on ice. The micelle fraction recovered as a precipitate from ultracentrifugation (80,000 rpm, 1 hour, 4° C., MLA-80 Rotor by Beckman Coulter) was suspended in 20 mM sodium phosphate buffer (pH 7.4)/5% glucose, and then washed by the same ultracentrifugation procedure, resuspended in the same buffer solution and provided for the following rat administration test.

Six-week-old Wistar male rats were divided into groups of 3 rats each, and the test solution was administered through the tail vein at a dosage of 10 mg/kg of FITC-labeled lysozyme. 5 minutes and 1, 3, 6, 9 and 24 hours after administration, about 0.2 mL of blood was collected from the cervical vein using a heparin-coated syringe. The blood was immediately centrifuged at 4° C. (EF-1300, ECO-Fuge™, Tomy Seiko Co., Ltd.) and the plasma was harvested and stored at −30° C. until analysis. A FITC-labeled lysozyme solution (20 mM sodium phosphate buffer, pH 7.4/5% glucose) was also tested in the same manner. The blood plasma concentration was measured by HPLC the following HPLC conditions.

System: Waters Alliance System

Column: Tosoh TSK-gel Super SW3000 (4.6ϕ×300 mm) (30° C.)

Mobile phase: 20 mM sodium phosphate buffer (pH 7.4)

Flow rate: 0.25 mL/min

Detection: Fluorescence (Ex: 492 nm, Em: 520 nm)

Injection volume; 10 µL

Figure 3:
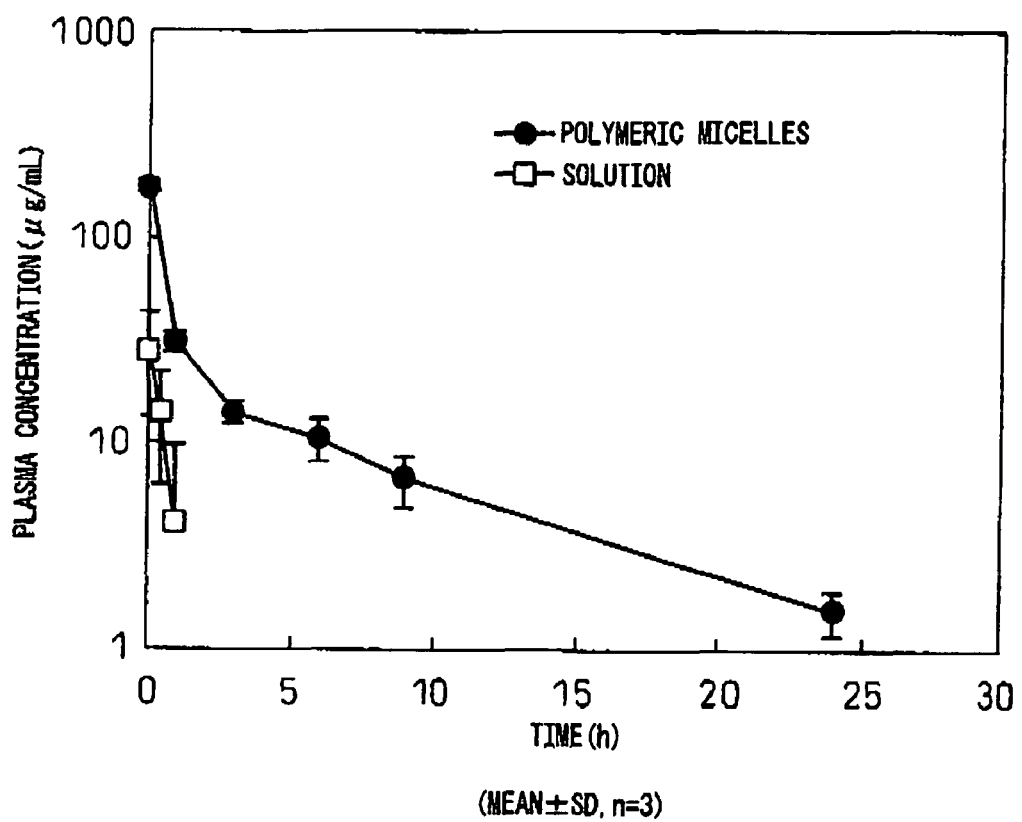
FIG. 3 shows a time-course of FITC-labeled lysozyme plasma concentration after intravenous administration of FITC-labeled lysozyme-encapsulating polymer micelles or FITC-labeled lysozyme solution to rats.

The results are shown in FIG. 3. The AUC increased approximately 15-fold by micellation compared to administration of the solution alone. These results indicate that the protein encapsulated in the micelles stay in the blood circulation for a long time without initial burst.

Example 11

Intravenous Administration Test with Interferon-α-Encapsulated Micelles 2

The block copolymer used was polyethylene glycol-co-polyaspartic acid dodecyl ester (hereinafter, PEG-PDLA. In this polymer, the aspartic acid residues without dodecyl esters are of general formula (I) wherein $R_5$ is —O— and $R_6$ is hydrogen (same hereunder)), or polyethylene glycol-co-polyaspartic acid hexadecyl ester (hereinafter, PEG-PHLA. The aspartic acid residues without hexadecyl esters are of the same general formula wherein $R_5$ is —O— and $R_6$ is hydrogen (same hereunder)). After precisely weighing out 200 mg of PEG-PDLA 12-40(65) or PEG-PHLA 12-40(65) into a glass vial, 10 mL of 20 mM MES buffer (pH 5.0) was added and the mixture was vigorously stirred overnight at 4° C. The polymer dispersion was subjected to ultrasonic treatment for about 15 minutes (1 second intermission, output: Low) using a Biodisruptor (High Power Unit, product of Nissei Corp.) while cooling on ice, to obtain an empty micelle solution with a polymer concentration of 20 mg/ml. A 0.65 mL portion of the empty micelle solution was transferred to a microtube (Ieda Chemicals Co., Ltd.), and then 65 µL of a recombinant human interferon-α PBS solution (IFN-α, PBL Biomedical Laboratories) and 50 µL of 0.1 M MES buffer (pH 5.0) were added and the mixture was carefully pipetted and then allowed to stand at 4° C. for 4 days. It was then rinsed with a 5% glucose solution using an ultrafiltration unit [AMICON® ULTRA-4 by Millipore (molecular cutoff: 100,000)] and concentrated for use in the following animal experiment.

Six-week-old Wistar rats were divided into groups of 3 rats each, and the test solution was administered through the tail vein at a dosage of 1×10⁶ IU/kg. 5 minutes and 1, 3, 6 and 24 hours after administration, about 0.2 mL of blood was collected from the cervical vein using a heparin-coated syringe. The blood was immediately centrifuged at 13,800 rpm, 4° C. (EF-1300, ECO-Fuge™, Tomy Seiko Co., Ltd.) and the plasma was harvested and stored at −30° C. until analysis. The plasma concentration of interferon-α was determined by a human interferon-α ELXSA kit (PBL Biomedical Laboratories).

Figure 4:
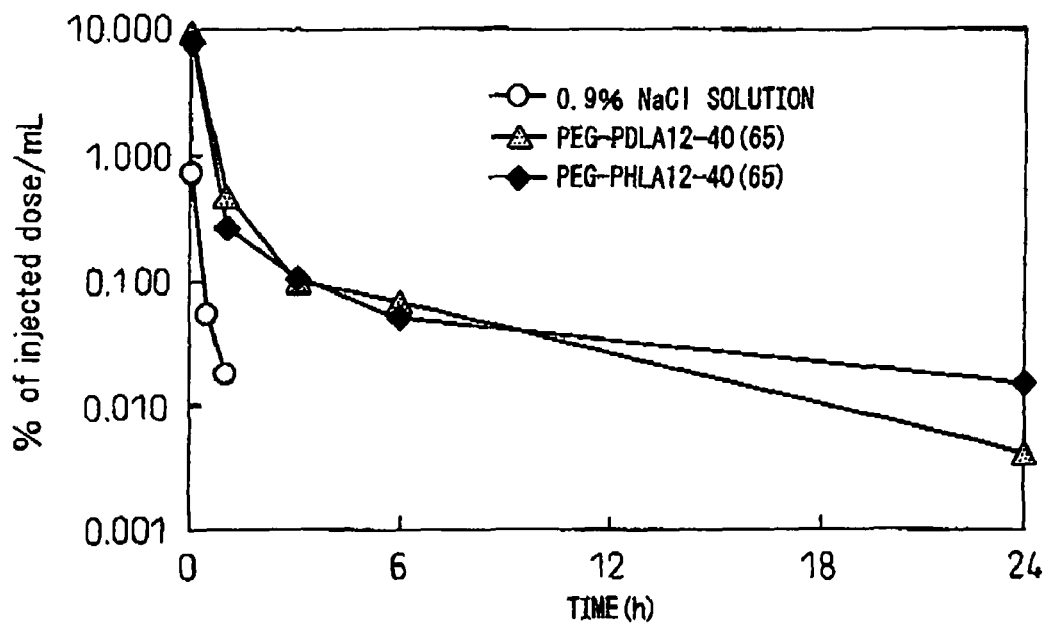
FIG. 4 shows a time-course of interferon-α plasma concentration after intravenous administration of interferon-α-encapsulating polymer micelles or interferon-α solution to rats.

FIG. 4 shows time-course of plasma concentration of interferon-α after administration of interferon-α-encapsulating polymer micelles. The AUC was enhanced by 32-fold when using PEG-PDLA 12-40(65) polymeric micelles and 27-fold when using PEG-PHLA 12-40(65) polymeric micelles compared with the solution alone.

Example 12

Intravenous Administration Test with Interferon-α-Encapsulated Micelles 3

The block copolymer used was polyethylene glycol-co-polyglutamic acid octyl ester (hereinafter, PEG-POLG. In this polymer, the glutamic acid residues without octyl esters are of general formula (I) wherein $R_5$ is —O— and $R_6$ is hydrogen (same hereunder)). After precisely weighing out 150 mg of PEG-POLG 12-40(65) into a glass vial, 5 mL of 20 mM MES buffer (pH 5.0) was added and the mixture was vigorously stirred overnight at 4° C. The polymer dispersion was subjected to ultrasonic treatment for about 15 minutes (1 second intermission, output: Low) using a Biodisruptor (High Power Unit, product of Nissei Corp.) while cooling on ice, to obtain an empty micelle solution with a polymer concentration of 30 mg/mL. A 0.6 mL portion of the empty micelle solution was transferred to a Cryovial (Ieda Chemicals Co., Ltd.), and then 90 μL of a recombinant human interferon-α solution (IFN-α, PBL Biomedical Laboratories) and 110 μL of 0.1 M MES buffer (pH 5.0) were added and the mixture was carefully pipetted and then allowed to stand at 4° C. for 3 days. A 400 μl portion thereof was then injected into a microtube, 20 mM MES buffer (pH 5.0) was added to 500 μL, and the mixture was rinsed with a 5% glucose solution using an ultrafiltration unit [AMICON™ ULTRA-4 by Millipore (molecular cutoff: 100,000)] and concentrated for use in the following animal experiment.

Six-week-old Wistar rats were divided into groups of 2 rats each, and the test solution was administered through the tail vein at a dosage of $1 \times 10^6$ IU/kg. 5 minutes and 1, 3, 6 and 24 hours after administration, about 0.2 mL of blood was collected from the cervical vein using a heparin-coated syringe. The blood was immediately centrifuged at 13,800 rpm, 4° C. (EF-1300, ECO-Fuge™, Tomy Seiko Co., Ltd.) and the plasma was harvested and stored at −30° C. until analysis. The plasma concentration of interferon-α was determined by a human interferon-α ELISA kit (PBL Biomedical Laboratories).

Figure 5:
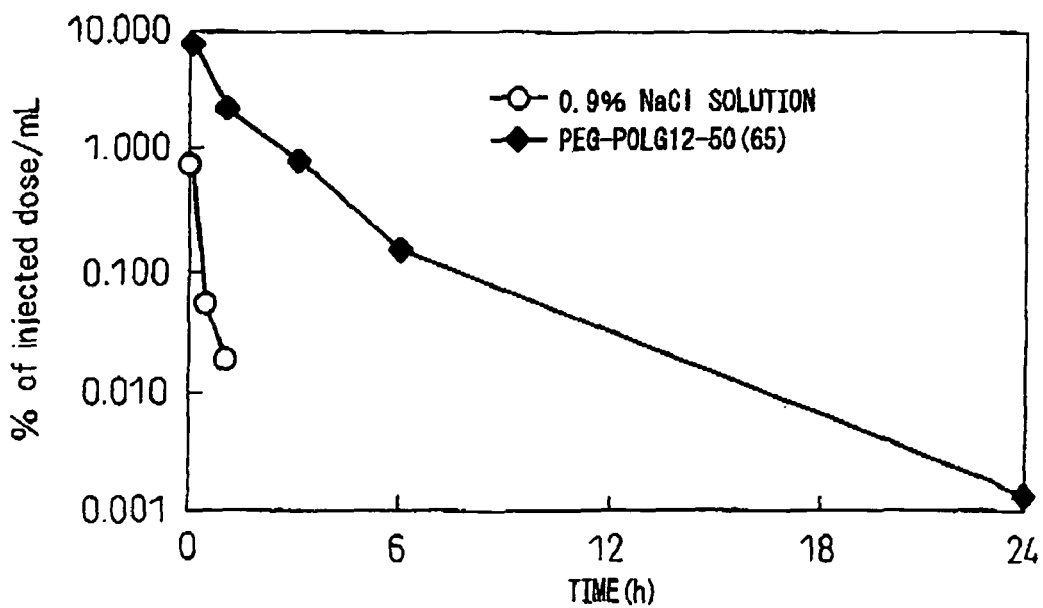
FIG. 5 shows a time-course of interferon-α plasma concentration after intravenous administration of interferon-α-encapsulating polymer micelles or interferon-α solution to rats.

FIG. 5 shows the time-course of plasma concentration of interferon-α after administration of interferon-α-encapsulating polymer micelles. Micellation increased the AUC by 57-fold.

Example 13

Preparation of Mellitin-Encapsulating Micelles

The block copolymer used was PEG-POLA 12-40(65) or PEG-POLG 12-40(65). After precisely weighing out 150 mg of polymer into a glass vial, 5 mL of 20 mM sodium phosphate buffer (pH 7.4) was added and the mixture was vigorously stirred at 4° C. The polymer dispersion was subjected to ultrasonic treatment for about 15 minutes (1 second intermission, output: Low) using a Biodisruptor (High Power Unit, product of Nissei Corp.) while cooling on ice, to obtain an empty micelle solution with a polymer concentration of 30 mg/mL. After then adding 20 mM sodium phosphate buffer (pH 7.4) for adjustment to 10 mg/mL (1 mL), the basic polypeptide mellitin (Sigma-Aldrich Corp.) (1 mg) was added, and the mixture was allowed to stand overnight at 4° C. and then subjected to gel filtration (Sepharose® CL-4B, GE Healthcare Bioscience, 1φ×30 cm). The mellitin concentration in each recovered fraction (eluent: 20 mM sodium phosphate buffer (pH 7.4), flow rate: 1.0 mL/min, fraction volume: 1 mL) was assayed using a BCA Protein Assay (Pierce Corp.) The encapsulation efficiency was calculated by the following formula.

$$\text{Encapsulation efficiency (\%)} = \frac{\text{(Protein content in micelle fraction)} \times 100}{\text{Total protein content in all fractions}}$$

The encapsulation efficiency was 71% for PEG-POLA 12-40(65) and 48% for PEG-POLG 12-40(65). The results indicate that polypeptides with molecular weights of approximately 2,800 can be efficiently encapsulated.

Example 14

Rat Intravenous Administration Test with Human Granulocyte Colony Stimulating Factor-Encapsulating Micelles 1

The block copolymer used was polyethylene glycol-co-polyaspartic acid octylamide (hereinafter, PEG-PONLA. This polymer comprises 50% of an amino acid residue of general formula (I) wherein $R_5$ is —NH— and $R_6$ is an octyl group, and 50% of an amino acid residue wherein $R_5$ is —NH— and $R_6$ is an amino group-substituted octyl group (same hereunder)). After precisely weighing out 30 mg of PEG-PONLA 12-40(50) into a glass vial, 2 mL of 5% glucose-containing 20 mM phosphate buffer (pH 7.4) was added, and then a Biodisruptor (High Power Unit, product of Nissei Corp.) was used for sonication for about 10 minutes (1 second intermission, output: Low) while cooling on ice, to prepare empty micelles. Recombinant human granulocyte colony stimulating factor (G-CSF, Green Cross) (pI: approximately 6.0) (300 μg/mL, 1 ml) was added and the mixture was allowed to stand for a full day at 4° C. The non-encapsulated G-CSF was then removed using an ultrafiltration unit (AMICON® ULTRA-4 by Millipore (molecular cutoff: 100,000)) to prepare micelles for the following animal experiment.

Six-week-old Wistar male rats were divided into groups of 3 rats each (6 rats per group for the solution alone), and the test solution was administered through the tail vein at a dosage of 100 μg/kg of the test solution. 5 minutes and 1, 3, 6 and 24 hours after administration, about 0.2 mL of blood was collected from the cervical vein using a heparin-coated syringe. The sample was immediately centrifuged at 13,800 rpm, 4° C. (EF-1300, ECO-Fuge™, Tomy Seiko Co., Ltd.) and the plasma was harvested and stored at −30° C. until analysis. A RayBio® Human G-CSF ELISA kit (RayBiotech Inc.) was used for plasma concentration assay.

Figure 6:
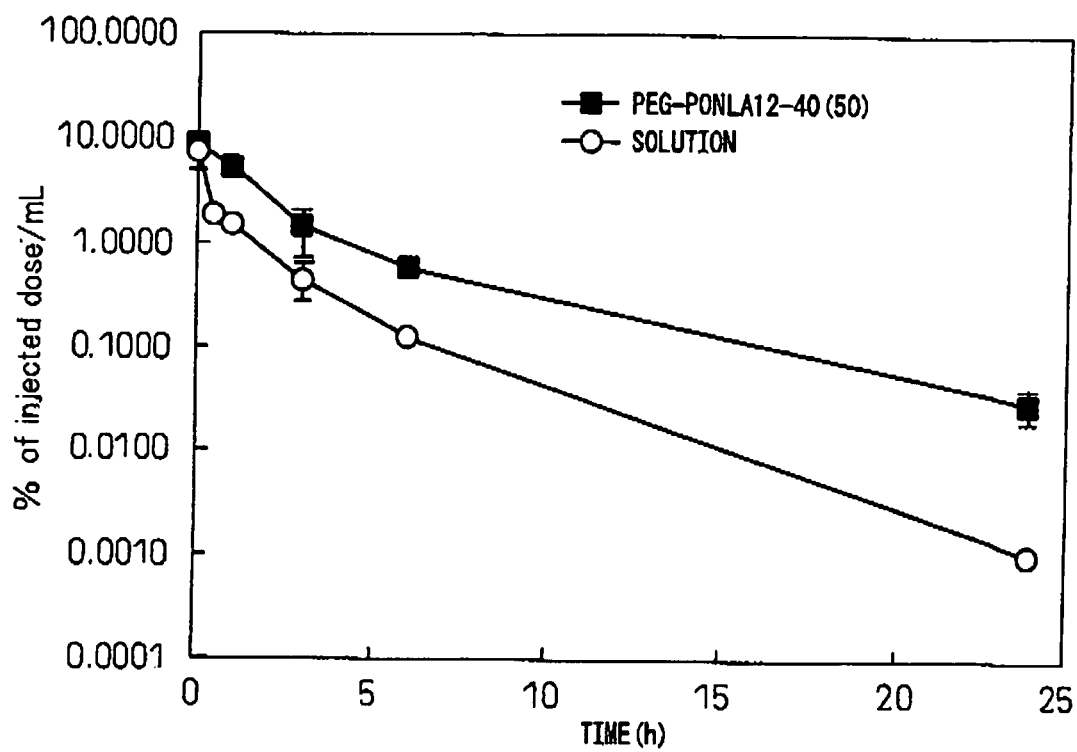
FIG. 6 shows a time-course of human granulocyte colony stimulating factor plasma concentration after intravenous administration of human granulocyte colony stimulating factor-encapsulating polymer micelles or human granulocyte colony stimulating factor solution to rats.

The assay results are shown in FIG. 6, and the pharmacokinetic parameters calculated according to a non-compartment model are shown in Table 2. Micellation increased the AUC by 3-fold, and prolonged the half-life by 2-fold.

TABLE 2

Pharmacokinetic parameters for human granulocyte colony stimulating factor-encapsulating polymer micelles or human granulocyte colony stimulating factor solution after intravenous administration to rats.

| Pharmacokinetic parameters | Solution | PEG-PONLA 12-40(50) micelles |
|---|---|---|
| $AUC_{inf}$ (% dose/mL · h) | 7.4 | 22 |

TABLE 2-continued

Pharmacokinetic parameters for human granulocyte colony stimulating factor-encapsulating polymer micelles or human granulocyte colony stimulating factor solution after intravenous administration to rats.

| Pharmacokinetic parameters | Solution | PEG-PONLA 12-40(50) micelles |
|---|---|---|
| $T_{1/2}$ (h) | 2.6 | 4.1 |
| Cl (mL/h/body) | 13 | 4.4 |
| $MRT_{inf}$(h) | 1.9 | 2.8 |
| Vss (mL/body) | 25 | 13 |

Example 15

Rat Intravenous Administration Test with Human Granulocyte Colony Stimulating Factor-Encapsulating Micelles 2

The block copolymer used was PEG-POLG. After precisely weighing out 30 mg of PEG-POLG 12-40(65) into a glass vial, 2 mL of 20 mM MES buffer (pH 5.0) was added, and then a Biodisruptor (High Power Unit, product of Nissei Corp.) was used for sonication for about 10 minutes (1 second intermission, output: Low) while cooling on ice, to prepare empty micelles. A recombinant human G-CSF solution (Green Cross) (300 μg/mL, 1 mL) was added and the mixture was allowed to stand for a day at 4° C. The non-encapsulated G-CSF was then removed using an ultrafiltration unit [AMICON® ULTRA-4 by Millipore (molecular cutoff: 100,000)] and diluted with 5% glucose-containing 20 mM phosphate buffer (pH 7.4) for use as micelles for an animal experiment. The micelles were intravenously administered to the rats at a dosage of 100 μg/mL in terms of G-CSF, in the same manner as Example 12. Blood was collected and the plasma concentration was assayed in the same manner.

Figure 7:
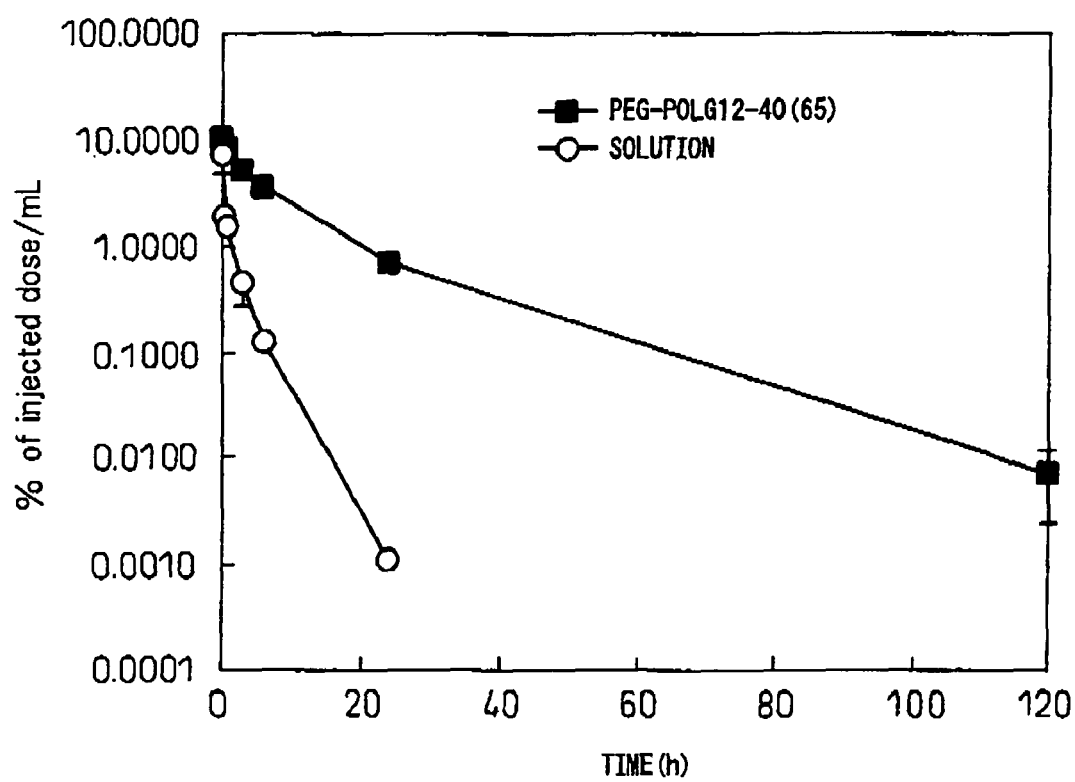
FIG. 7 shows a time-course of human granulocyte colony stimulating factor plasma concentration after intravenous administration of human granulocyte colony stimulating factor-encapsulating polymer micelles or human granulocyte colony stimulating factor solution to rats.

The results are shown in FIG. 7, and the pharmacokinetic parameters calculated according to a non-compartment model are shown in Table 3. Encapsulation in polymeric micelles of human granulocyte increased the AUC by 15-fold and prolonged the half-life by 5-fold compared with the solution, and the plasma concentration was still detectable even 120 hours after administration. These results indicate that the protein-encapsulating micelles 5 stay in the blood circulation for a long time without initial burst.

TABLE 3

Pharmacokinetic parameters for human granulocyte colony stimulating factor-encapsulating polymer micelles or human granulocyte colony stimulating factor solution after intravenous administration to rats.

| Pharmacokinetic parameters | Solution | PEG-POLG 12-40(65) micelles |
|---|---|---|
| $AUC_{inf}$ (% dose/mL · h) | 7.4 | 111 |
| $T_{1/2}$ (h) | 2.6 | 14 |
| Cl (mL/h/body) | 13 | 0.90 |
| $MRT_{inf}$(h) | 1.9 | 12 |
| Vss (mL/body) | 25 | 11 |

The above explanation of the invention is intended merely to serve for concrete illustration. It is to be understood that various modifications thereto may be implemented such as are within the concept and scope of the invention. The claims are therefore intended to be interpreted as encompassing all such modifications.

What is claimed is:

1. A polymer micelle composition for encapsulating polypeptides or proteins, comprising:
a polypeptide or protein having a molecular weight of at least 20,000 daltons having an isoelectric point (pI); and
a block copolymer comprising hydrophilic segments composed of polyethylene glycol, and hydrophobic segments composed of a polyamino acid selected from the group consisting of acidic amino acids, hydrophobic derivatives thereof and mixtures of said acidic amino acids and said hydrophobic derivatives, the acidic amino acids and/or the hydrophobic derivatives having an isoelectric point (pI'), wherein the polypeptide or protein are combined with the block copolymer to form a micelle mixture, and the pH of the micelle mixture is:

pI>pH>pI' such that the hydrophobic segments of the block copolymer are negatively charged at the pH while the protein or polypeptide is positively charged, wherein the pH has a difference of at least 1 from the pI of the protein or polypeptide.

2. A composition according to claim 1, wherein the hydrophobic derivatives of the acidic amino acids are acidic amino acid alkyl esters or acidic amino acid alkylamides.

3. A composition according to claim 1, wherein the acidic amino acids are aspartic acid and glutamic acid.

4. A composition according to claim 1, wherein the block copolymer has the following formula (I) or (II):

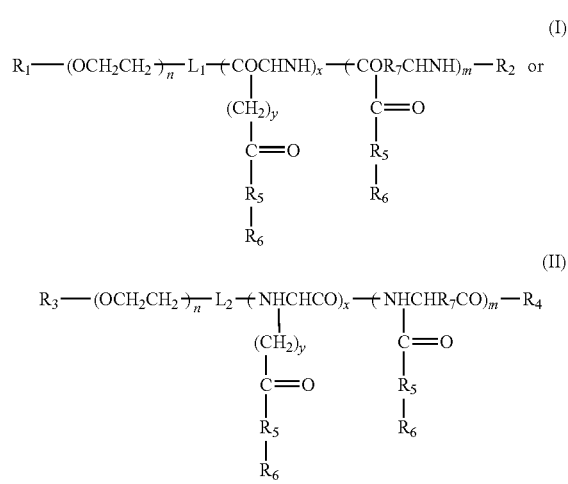

wherein, $R_1$ and $R_3$ each independently represent hydrogen or a lower alkyl group either unsubstituted or substituted with an optionally protected functional group, $R_2$ represents hydrogen, a saturated or unsaturated $C_1$-$C_{29}$ aliphatic carbonyl group or an arylcarbonyl group, $R_4$ represents hydroxyl, a saturated or unsaturated $C_1$-$C_{30}$ aliphatic oxy or aryl-lower alkyloxy group, $R_5$ represents —O— or —NH—, $R_6$ represents hydrogen, phenyl, —$(CH_2)_4$— phenyl, $C_4$-$C_{16}$ alkyl either unsubstituted or substituted with an amino group or carboxyl group, or benzyl, $R_7$ represents methylene, n represents an integer of 10-2500, x represents an integer of 10-300, m represents an integer of 0-300, with the proviso that when m is present, the (COCHNH) units and (COR$_7$CHNH) units are random, $R_6$ may be selected for each amino acid unit in one block copolymer and is randomly present, but hydrogen as $R_6$ constitutes less than 60% of the total $R_6$, y represents an integer of 1 or 2, $L_1$ represents a linking group selected from the group consisting of —NH—, —O—, —O—Z—NH—, —CO—, —CH$_2$—, —O—Z—S—Z— and —OCO—Z—NH—, where each Z independently represents a $C_1$-$C_6$ alkylene group, and $L_2$ represents a linking group selected from the group consisting of —OCO—Z—CO— and —NHCO—Z—CO—, where Z is a $C_1$-$C_6$ alkylene group.

5. A composition according to claim 4, wherein the block copolymer has a polyamino acid side chain esterification or amidation rate of 40-100%.

6. A composition according to claim 1, wherein the isoelectric point (pI) of the protein or polypeptide is 3-11.5.

7. A method of preparing a polymer micelle composition according to claim 1, comprising:

mixing the block copolymer with the protein or polypeptide: and adjusting the pH of the mixture to a pH that is pI>pH>pI', wherein the pH has a difference of at least 1 from the pI of the protein or polypeptide.

8. The composition of claim 1, wherein the amount of polypeptide or protein encapsulated in the polymer micelle is increased compared to the amount of polypeptide or protein encapsulated in a polymer micelle having a pH that is not pI>pH>pI'.

9. The composition of claim 1, wherein the amount of polypeptide or protein encapsulated in the polymer micelle is increased compared to the amount of polypeptide or protein encapsulated in a polymer micelle at a pH equal to the pI of the polypeptide or protein.

\* \* \* \* \*